United States Patent [19]

Soelberg et al.

[11] 4,265,623

[45] May 5, 1981

[54] CLAMP FOR A DENTAL DAM

[75] Inventors: Kenneth B. Soelberg, Menlo Park; Marvin M. Stark, Los Altos Hills, both of Calif.; Tommy H. Thompson, Missoula, Mont.; Akia Yamaguchi, Los Angeles, Calif.

[73] Assignee: Marvin M. Stark Research Foundation, Santa Clara, Calif.

[21] Appl. No.: 120,009

[22] Filed: Feb. 8, 1980

[51] Int. Cl.³ .............................................. A61C 5/12
[52] U.S. Cl. ..................................................... 433/139
[58] Field of Search ........................................ 433/139

[56] References Cited

U.S. PATENT DOCUMENTS

| | | | |
|---|---|---|---|
| 412,622 | 10/1889 | Ivory | 433/139 |
| 1,336,746 | 4/1920 | Ivory | 433/139 |

*Primary Examiner*—Robert Peshock
*Attorney, Agent, or Firm*—Lothrop & West

[57] ABSTRACT

A dental dam clamp in each of two lateral wings has an aperture at least partially bounded by several arcuate walls to engage a handling tool in any of several different positions.

6 Claims, 5 Drawing Figures

CLAMP FOR A DENTAL DAM

BRIEF SUMMARY OF THE INVENTION

A dental dam clamp having a pair of substantially coplanar lateral wings joined at one end by an upstanding bridge has substantially similar tool apertures in each of said wings, the apertures being generally symmetrical with each other and being defined at least in part by a plurality of substantially intersecting, arcuate walls so as to receive a handling tool (clamp or forceps) in any of several different positions.

DETAILED DESCRIPTION

In dental work, it is very often necessary to surround one or more of the patient's teeth with a flexible dam, usually a sheet of rubber-like material, in order that the operative field may be kept relatively uncontaminated and relatively dry. The dam is customarily retained in position temporarily against and at least partially around a tooth by an appropriate clamp of somewhat springy material, usually metal. The clamp presses the rubber-like dam material against the tooth surface sufficiently well as to preclude fluid flow therebetween. The custommary clamp is provided with a pair of generally circular holes through it, engageable by the customary tools, such as a pair of forceps or pincers. These are both during installation and during removal.

In many instances there is no difficulty in accomplishing the desired aims, but there are instances in which the patient's teeth are located with respect to each other and are so irregularly positioned that it is difficult indeed to accomplish the desired ends with the customary tools and often without substantial discomfort to the patient.

It is therefore an object of the invention to provide a clamp for dental use that is especially arranged so that the customarily used tools can be utilized with it but in an improved fashion so that there is little or no discomfort to the patient and so that the dentist's work is facilitated.

Another object of the invention is to provide a dental clamp of such a nature that, although improved, the manner of its use is apparent to a dentist without extensive extra instruction.

A further object of the invention is to provide a dental clamp that can be manufactured by the customary procedures and with only relatively inexpensive modification to the manufacturing tools.

A further object of the invention is in general to provide an improved dental clamp.

While the dental clamp pursuant to the invention can be embodied in a large number of different ways and can sometimes be especially embodied for extraordinarily difficult instances of use, it has with some success been utilized as disclosed herein in connection with difficult situations.

Figure 1:
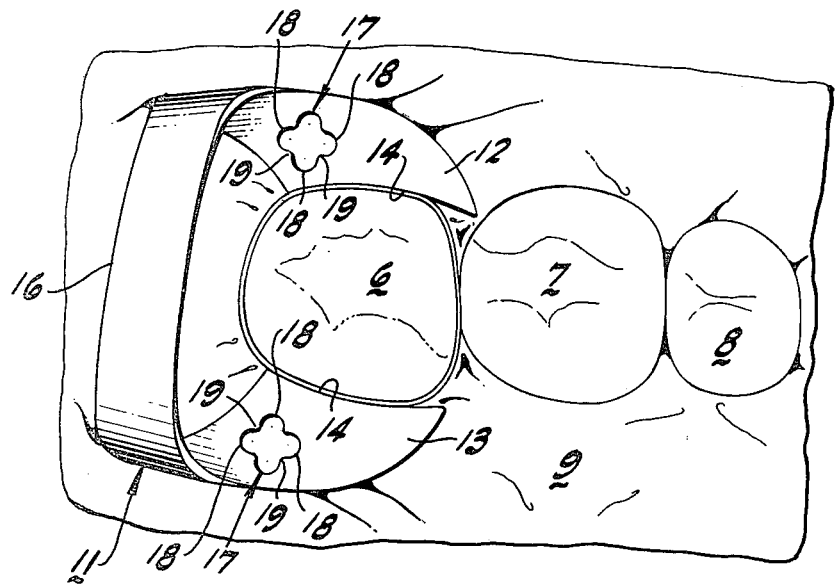
FIG. 1 is a plan, with portions broken away, of the clamp of the invention in use in a patient's mouth and engaging a flexible dental dam adjacent one of the teeth.

As particularly shown in FIG. 1, for example, the customary environment is in a patient's mouth having a number of adjacent teeth 6, 7 and 8 therein, at least one of which is to be treated.

In accomplishing this, it is appropriate to provide around one or more of the teeth a dental dam 9. This conveniently is a sheet of highly flexible, relatively thin, waterproof material of a generally rubber-like nature. The dam is perforated to accept piercing by the teeth 6, 7 and 8, yet is flexible and resilient enough so as to lie quite closely adjacent the surfaces of such teeth. The dam usually; for example, when used just above the lower jaw, extends upwardly and around much of the exposed, generally upstanding, exterior surface of the teeth.

In order to maintain the dam in such position during subsequent use, there is provided a clamp 11. This is usually of a ferrous metal containing a substantial portion of cobalt and chrome and itself is somewhat springy, although not affected adversely by autoclaving for disinfection. The clamp material is sheet-like itself and is in plan of approximately C-shape. There is a pair of lateral wings 12 and 13 lying substantially in a common plane and being substantially symmetrical about a longitudinal center line of the device. Each of the wings 12 and 13 has an interior arcuate surface 14 adapted to engage and lie against the upstanding portion of the dam 9. The wings 12 and 13 are also joined in a springy fashion by a transverse bridge 16, usually integral and extending to the rear and upwardly from the general plane occupied by the wings themselves.

Particularly pursuant to the present invention, each of the wings 12 and 13 is provided with a tool aperture 17 disposed substantially between the lateral portions of that wing and substantially midway between the fore and aft portions of the clamp.

In contradistinction to previous constructions, each of the tool apertures 17 is of a special configuration or shape. For example, as especially shown in FIGS. 1, 2 and 5, each of the tool apertures is defined by a related one of four semi-circular arcs 18. Each of the arcs lies on one side of an imaginary, inscribed square. With this construction, there results a plurality of cusps 19 between adjacent ones of the arcuate portions.

Preferably, the arcs 18 are not only of substantially semi-circular extent, but each has a radius that is slightly more, but only slightly more, than the radius of the circular cross-section jaws 21 (FIG. 4) of an appropriate handling tool 22 such as a forceps or clamp.

With this arrangement, even though the user's tooth, such as 6, may not be as regularly disposed as shown in FIG. 1, but may be inclined at any of a number of different angles, the dentist in utilizing his forceps 22 may put one of the prongs 21 in any one of the four arcuate portions on one side of the device; i.e., one of the wings, such as 12, and may then place the other one of the forcep prongs in an entirely differently located one of the arcuate portions of the opening in the wing 13. This is illustrated in two tool positions in FIG. 2. Thus, by having a plurality of tool-engaging surfaces in each of the apertures 17, and by changing the dimensions and location of such arcuate portions, it is possible for the dentist to utilize the standard tool in any one of a number of different locations to accommodate more readily variant positions and conditions in the patient's mouth.

Figure 3:
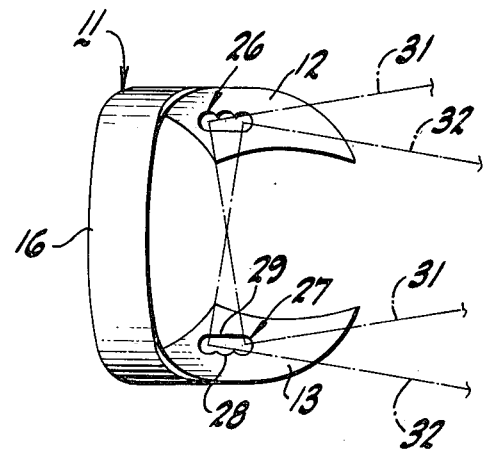
FIG. 3 is a view similar to FIG. 2 but showing apertures of different configurations.

In a somewhat similar fashion, as shown in FIG. 3, the tool apertures 26 and 27 therein are comprised of a number of approximately semi-circular, arcuate portions 28 arranged side by side, or intersecting, and having a common opposite boundary 29. In this instance, also, the tool, represented by the broken lines 31 and 32, can be disposed at different transverse angles to accommodate differently misplaced teeth.

Figure 4:
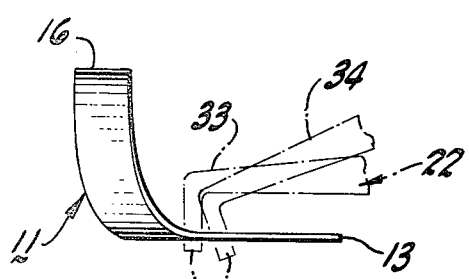
FIG. 4 is a side elevation of the structure of FIG. 2, for example, and various tool relationships therewith.

In addition, there is a further accommodation provided, as particularly shown in FIG. 4, in that the margins of the arcuate portions such as 17 and 28 are made with a curved cross-section or to extend at some angle to the general plane of the lateral portions 12 and 13 so that the jaws 21 of the tool need not be only in the perpendicular position 33, as shown in FIG. 4, but can rather be in the inclined position 34 as shown in that figure. This alternative position also assists the dentist in taking into account various extraordinary position angles of the tooth being worked on.

Figure 2:
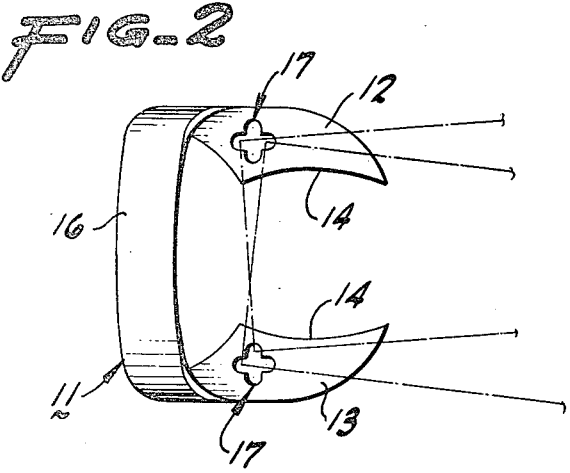
FIG. 2 is a plan similar to FIG. 1 of the clamp by itself and indicating various positions of a tool relative thereto.
Figure 5:
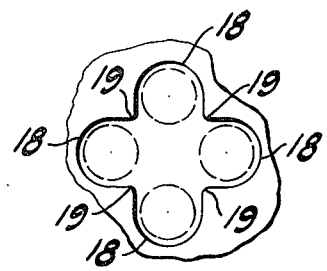
FIG. 5 is an enlarged view similar to a portion of FIG. 2 showing different positions of a tool relative to the clamp.

While, as shown in FIG. 3, there are three distinct possible tool positions on each side of the device and, as shown in FIGS. 2 and 5, there are four such possible positions, it is to be understood that the arrangement, as shown in FIG. 5, can also be of a trefoil contour instead of a quatrefoil contour and also that the arrangement of FIG. 3 can have four or more, or perhaps only two, of the arcuate portions 28.

By use of a device as disclosed herein, with the ordinary or normal dental tools it is possible to provide a good clamping action against a dental dam even though the tooth with which the clamp is utilized is far out of normal position. The present clamp is equally useful in connection with teeth that have a standard position.

We claim:

1. A clamp for a dental dam of flexible material adapted at least partially to surround and extend along the surface of a tooth, said clamp comprising:
   a. a substantially C-shaped springy member including a pair of lateral, substantially planar wings adapted to abut the lateral portions of said dam;
   b. a bridge upstanding from and joined to said wings; and,
   c. means defining a pair of tool apertures, one in each of said wings, the margins of each of said apertures having a shape and size such that the nose of a tool inserted therein can be moved to a number of different tool positions in the plane of said wings for close engagement with at least a portion of said margins in each of said different tool position.

2. A dental dam clamp as in claim 1 in which said margins of each of said apertures define at least in part a plurality of arcs each adapted to engage a substantial portion of the nose of a tool inserted therein.

3. A clamp as in claim 2 in which said arcs are each substantially semi-circular and intersect each other.

4. A clamp as in claim 3 in which said arcs form a trefoil contour.

5. A clamp as in claim 2 in which said arcs form a quatrefoil contour.

6. A clamp as in claim 1 in which at least a portion of said margins is inclined relative to the plane of said wings in order closely to engage the use of a tool inserted therein at said angle.

* * * * *